US012630849B2

(12) United States Patent
Asahi et al.

(10) Patent No.: US 12,630,849 B2
(45) Date of Patent: May 19, 2026

(54) METHOD FOR PRODUCING POLYPHENOL-CONTAINING COMPOSITION

(71) Applicant: Toray Industries, Inc., Tokyo (JP)

(72) Inventors: Yuka Asahi, Kamakura (JP); Atsushi Minamino, Udon Thani (TH); Satoru Itou, Udon Thani (TH)

(73) Assignee: Toray Industries, Inc., Tokyo (JP)

( * ) Notice: Subject to any disclaimer, the term of this patent is extended or adjusted under 35 U.S.C. 154(b) by 340 days.

(21) Appl. No.: 18/285,082

(22) PCT Filed: Mar. 29, 2022

(86) PCT No.: PCT/JP2022/015547
§ 371 (c)(1),
(2) Date: Sep. 29, 2023

(87) PCT Pub. No.: WO2022/210733
PCT Pub. Date: Oct. 6, 2022

(65) Prior Publication Data

US 2024/0175061 A1 May 30, 2024

(30) Foreign Application Priority Data

Mar. 30, 2021 (JP) ................................. 2021-058651

(51) Int. Cl.

| | |
|---|---|
| A23L 35/00 | (2016.01) |
| C07C 45/79 | (2006.01) |
| C07G 1/00 | (2011.01) |
| C12N 9/24 | (2006.01) |
| C12P 7/22 | (2006.01) |
| C12P 7/44 | (2006.01) |

(52) U.S. Cl.
CPC ............. *C12P 7/22* (2013.01); *C12P 2201/00* (2013.01)

(58) Field of Classification Search
CPC ... A23L 35/00; C07G 1/00; C12P 7/22; C07C 45/79
See application file for complete search history.

(56) References Cited

U.S. PATENT DOCUMENTS

| | | |
|---|---|---|
| 2016/0081381 A1 | 3/2016 | Medoff |
| 2016/0145183 A1 | 5/2016 | Revelant et al. |
| 2019/0100776 A1 | 4/2019 | Funada et al. |
| 2021/0369597 A1 | 12/2021 | Furuta et al. |

FOREIGN PATENT DOCUMENTS

| | | | |
|---|---|---|---|
| CA | 3085730 | * | 6/2019 |
| JP | 2013-220067 A | | 10/2013 |
| JP | 2016-520093 A | | 7/2016 |
| JP | 2017-530701 A | | 10/2017 |
| JP | 2020-093080 A | | 6/2020 |
| WO | 2006/013530 A1 | | 2/2006 |
| WO | 2012/120184 A2 | | 9/2012 |
| WO | 2017/154955 A1 | | 9/2017 |
| WO | 2017/170549 A1 | | 10/2017 |
| WO | 2018/079640 A1 | | 5/2018 |
| WO | 2018/079641 A1 | | 5/2018 |
| WO | 2019/230803 A1 | | 12/2019 |

OTHER PUBLICATIONS

Michael J. Selig et al., "Synergistic enhancement of cellobiohydrolase performance on pretreated corn stover by addition of xylanase and esterase activities," Bioresource Technology, vol. 99, 2008, pp. 4997-5005.
Rui Zhao et al., "Integration of a phenolic-acid recovery step in the CaCCO process for efficient fermentable-sugar recovery from rice straw," Bioresource Technology, vol. 148, 2013, pp. 422-427.
International Search Report dated Jun. 14, 2022 in counterpart International Application No. PCT/JP2022/015547 w/English translation.
Written Opinion dated Jun. 14, 2022 in counterpart International Application No. PCT/JP2022/015547.

* cited by examiner

*Primary Examiner* — Maryam Monshipouri
(74) *Attorney, Agent, or Firm* — DLA Piper LLP (US)

(57) ABSTRACT

A method of producing a polyphenol-containing composition derived from herbaceous biomass includes: (1) bringing the herbaceous biomass into contact with an alkaline aqueous solution to obtain an extract; (2) adjusting pH of the extract obtained in step (1) to 3.2 or more and 4.5 or less and reacting the extract with an enzyme having cellobiohydrolase activity and xylanase activity to obtain an enzyme reaction solution; and (3) subjecting the enzyme reaction solution obtained in step (2) to solid-liquid separation to obtain a clear liquid containing a polyphenol-containing composition.

4 Claims, No Drawings

METHOD FOR PRODUCING POLYPHENOL-CONTAINING COMPOSITION

TECHNICAL FIELD

This disclosure relates to a method of producing a polyphenol-containing composition from herbaceous biomass.

BACKGROUND

In recent years, utilization of biomass has attracted attention due to problems of global warming and depletion of oil resources, as well as from the viewpoint of carbon neutrality. One of methods thereof is a method of producing a polyphenol composition from cellulose-containing biomass that does not compete with food.

The cellulose-containing biomass is mainly composed of polysaccharides, cellulose and hemicellulose, and an aromatic polymer, lignin. The lignin and connections between the lignin and the polysaccharides in the cellulose-containing biomass are decomposed to yield a decomposition liquid containing polyphenols.

For example, WO 2017/170549 describes a method of passing an alkaline aqueous medium through cellulose-containing biomass to efficiently obtain hydroxycinnamic acid, and WO 2012/120184 describes a method of recovering acid-insoluble lignin from an alkaline extract of a plant. In addition, WO 2019/230803 describes a method of efficiently producing a polyphenol composition through filtering an extract obtained by treating bagasse, which is a residue of pressed sugar cane, with an alkaline solution after adjusting the extract to be acidic, and adsorbing a filtrate thereof with an aromatic synthetic adsorbent.

Conventionally, such alkali treatment of cellulose-containing biomass has been carried out as a pretreatment to make it easier to obtain a sugar liquid from the cellulose-containing biomass, and the liquid after the alkali treatment has been disposed of. However, effective utilization thereof is desired because the liquid contains the polyphenol content as described above.

The decomposition liquid containing polyphenols obtained by the above-described conventional techniques is known to be used as, for example, a deodorant (Japanese Patent Laid-Open No. 2020-93080), a food discoloration inhibitor (WO 2018/079640), and an aquatic organism growth promotor (WO 2018/079641). It is also known that typical polyphenols contain coumaric acid and ferulic acid.

As described above, a conventional method of efficiently producing a polyphenol-containing composition from herbaceous biomass includes a method of subjecting a pretreatment liquid obtained by treating herbaceous biomass with an alkaline solution to solid-liquid separation after adjusting the liquid to be acidic. However, we found that the solid-liquid separation is poorly achieved, or a micelle-like phenomenon occurs to thereby prevent solid-liquid separation in some instances. Moreover, we found that filtration performance may also poor in a separation membrane treatment applied to purification and concentration of a liquid after the solid-liquid separation.

Therefore, it could be helpful to provide novel technical means of efficiently producing a polyphenol-containing composition from herbaceous biomass.

SUMMARY

We found that a polyphenol-containing composition can be efficiently produced from herbaceous biomass by adjusting pH of an alkali-treated extract of the herbaceous biomass and reacting the extract with a specific enzyme.

We thus provide [1] to [13]:

[1] A method of producing a polyphenol-containing composition derived from herbaceous biomass, the method including:

(1) bringing the herbaceous biomass into contact with an alkaline aqueous solution to obtain an extract;

(2) adjusting pH of the extract obtained in step (1) to 3.2 or more and 4.5 or less and reacting the extract with an enzyme having cellobiohydrolase activity and xylanase activity to obtain an enzyme reaction solution; and (3) subjecting the enzyme reaction solution obtained in step (2) to solid-liquid separation to obtain a clear liquid containing a polyphenol-containing composition.

[2] The method according to [1], wherein the pH of extract obtained in the step (1) is adjusted to 3.5 or more and less than 4.0.

[3] The method according to [1] or [2], wherein the alkaline aqueous solution used in the step (1) is at 60° C. or higher.

[4] The method according to any one of [1] to [3], further including:

(4) filtering the clear liquid obtained in the step (3) through one or more separation membranes selected from the group consisting of a microfiltration membrane, an ultrafiltration membrane, a nanofiltration membrane, and a reverse osmosis membrane to obtain a permeate and/or non-permeate containing the polyphenol-containing composition.

[5] The method according to [4], wherein the microfiltration membrane is used as a separation membrane to obtain a permeate containing the polyphenol-containing composition.

[6] The method according to [4] or [5], wherein the permeate obtained by filtering the clear liquid through a microfiltration membrane in step (4) is filtered through one or more separation membranes selected from the group consisting of an ultrafiltration membrane, a nanofiltration membrane, and a reverse osmosis membrane to collect the non-permeate containing the polyphenol-containing composition.

[7] The method according to any one of [4] to [6], wherein the clear liquid or the permeate obtained by filtration through a microfiltration membrane in the step (4) is filtered through a nanofiltration membrane to obtain a permeate containing the polyphenol-containing composition.

[8] The method according to [7], wherein the nanofiltration membrane has a molecular weight cut-off of 300 to 1,000.

[9] The method according to any one of [1] to [8], wherein a reaction time of the enzyme in the step (2) is 10 minutes to 2 hours.

[10] The method according to any one of [1] to [9], wherein the herbaceous biomass is bagasse.

[11] The method according to any one of [1] to [10], wherein the enzyme is derived from a microorganism belonging to the genus *Trichoderma*.

[12] A polyphenol-containing composition containing coumaric acid and xylose, wherein a content of the xylose relative to the coumaric acid is 1 to 200% (w/w).

[13] The polyphenol-containing composition according to [12], wherein the content of the xylose relative to the coumaric acid is 2 to 50% (w/w).

A polyphenol-containing composition can thus be efficiently produced from herbaceous biomass. In the production of the polyphenol-containing composition from herbaceous biomass, we prevent a micelle-like phenomenon and increase the efficiency of solid-liquid separation. We also improve filtration performance of a product formed after the solid-liquid separation in the separation membrane treatment.

DETAILED DESCRIPTION

According to an example, a method of producing a polyphenol-containing composition from herbaceous biomass includes:

(1) bringing the herbaceous biomass into contact with an alkaline aqueous solution to obtain an extract;

(2) adjusting pH of the extract obtained in step (1) to 3.2 or more and 4.5 or less and reacting the extract with an enzyme having cellobiohydrolase activity and xylanase activity to obtain an enzyme reaction solution; and (3) subjecting the enzyme reaction solution obtained in step (2) to solid-liquid separation to obtain a clear liquid containing a polyphenol-containing composition.

Hereinafter, examples of our methods are described.

Step (1)

According to an example, in the step (1), herbaceous biomass is brought into contact with alkaline aqueous solution to obtain an extract, as described above.

Examples of herbaceous biomass include, but are not limited to, bagasse, which is a residue of pressed sugar cane, switchgrass, napier grass, Erianthus, corn stover, corn husk, wheat husk, soybean husk, rice straw, wheat straw, and empty fruit bunch of oil palm. From the viewpoint of production of polyphenols, herbaceous biomass with a lignin content of 5% or more is preferably used. Specifically, bagasse, napier grass, Erianthus, corn stover, and rice straw are preferred, and bagasse is more preferred. The lignin content can be determined by measuring Klason lignin, which is the residue of acid hydrolysis minus ash.

The herbaceous biomass is not particularly limited in shape but is preferably subjected to a grinding treatment. The grinding means is not particularly limited, and grinding can be performed with a machine commonly used for coarse grinding of various materials such as a ball mill, a vibration mill, a cutter mill, a hammer mill, a Wiley mill, or a jet mill. This mechanical grinding may be either dry grinding or wet grinding, yet is preferably dry grinding.

The water content of the herbaceous biomass is not particularly limited, but a preferred range thereof is, for example, about 3% or more, about 3% or more and about 75% or less, about 5% or more, about 5% or more and about 70% or less, about 5% or more and about 65% or less, and about 5% or more and about 55% or less.

Polyphenols may include one or more of hydroxycinnamic acids such as coumaric acid and ferulic acid, and lignin degradants, which can be measured, for example, by the Folin-Ciocalteu method. The Folin-Ciocalteu method is originally developed for the purpose of analyzing aromatic amino acids such as tyrosine and tryptophan and proteins having these amino acids, in which blue color resulting from a phenolic hydroxy group reducing phosphotungstic acid and molybdic acid under alkaline conditions is colorimetrically determined at 700 to 770 nm. The same operation is performed using a specific reference substance such as gallic acid or catechin, and a quantitative value thereof can be shown in terms of the compound. The value in terms of catechin is used.

The alkaline aqueous solution may contain at least one selected from ammonia, aqueous ammonia, alkali metal hydroxide, alkali metal oxide, alkaline earth metal oxide, alkali metal carbonate, alkaline earth metal carbonate, quaternary ammonium hydroxide and the like, but is preferably an aqueous medium containing at least one hydroxide selected from sodium hydroxide and potassium hydroxide and more preferably an aqueous sodium hydroxide or aqueous potassium hydroxide.

The alkali concentration of the alkaline aqueous solution is not particularly limited but is 0.05% by weight or more and 10% by weight or less, preferably 0.05% by weight or more and 5% by weight or less, more preferably 0.1% by weight or more and 5% by weight or less, even more preferably 0.1% by weight or more and 3% by weight or less, and still more preferably 0.1% by weight or more and 2% by weight or less.

The lower limit of the pH of the alkaline aqueous solution is not particularly limited as long as it is alkaline, but is pH 7 or more, preferably pH 8 or more, more preferably pH 9 or more, and even more preferably pH 10 or more. The upper limit of the pH is not particularly limited as long as it is less than pH 14, but can be set to pH 12 or less from the viewpoint of reducing the amount of alkali used. A preferred pH range is, for example, 7 or more and 13.5 or less, or 8 or more and 13.5 or less; a more preferred pH range is 9 or more and 13.5 or less; and an even more preferred pH range is 10 or more and 12 or less.

The temperature at which the alkaline aqueous solution is brought into contact with the herbaceous biomass may be 60° C. or higher. To keep an alkali-treated product at a temperature higher than 100° C., it is necessary to apply a pressure exceeding the normal pressure to the alkali-treated product, which requires a high-pressure facility. Therefore, from the viewpoint of production cost, the temperature is preferably 60° ° C. to 100° C., more preferably 80° C. to 100° C., even more preferably 60° C. or higher and lower than 100° C., and 80° C. or higher and lower than 100° C.

The weight ratio of the alkaline aqueous solution to the herbaceous biomass (dry weight) is not particularly limited but preferably, for example, 100:1 to 2:1, 90:1 to 3:1, 50:1 to 5:1, 30:1 to 5:1, 25:1 to 7:1, 25:1 to 7:1, 25:1 to 5:1, or 20:1 to 5:1.

Examples of the method of bringing the herbaceous biomass into contact with the alkaline aqueous solution, but are not particularly limited, include spraying, immersing, or passing the alkaline aqueous solution into the herbaceous biomass, during which the alkaline aqueous solution and the herbaceous biomass may be stirred or a container thereof may be rotated to sufficiently contact them.

The contact time between the aqueous alkaline solution and the herbaceous biomass is not particularly limited, but is preferably about 20 minutes or more and about 72 hours or less, about 20 minutes or more and about 48 hours or less, about 20 minutes or more and about 24 hours or less, about 30 minutes or more and about 48 hours or less, about 30 minutes or more and about 24 hours or less, about 30 minutes or more and about 12 hours or less, about 30 minutes or more and about 6 hours or less, or about 30 minutes or more and about 3 hours or less.

The herbaceous biomass and the alkaline aqueous solution can be subjected to solid-liquid separation to obtain an extract. Examples of the solid-liquid separator include a screw press and a centrifugal separator. A strainer or the like may be used to remove fine particles. When the alkaline aqueous solution is passed through the herbaceous biomass at the time of the contact with each other, the liquid after passing may be used as the extract as it is, while squeezing a reactant of the herbaceous biomass with a solid-liquid separator is preferred from the viewpoint of recovery of the extract.

Step (2)

According to an example, in the step (2), pH of the extract obtained in the step (1) is adjusted to 3.2 or more and 4.5 or less, and the extract is reacted with an enzyme having cellobiohydrolase activity and xylanase activity to obtain an enzyme reaction solution.

An acidic substance may be added to the extract obtained in the above step to adjust the pH to the acidic range as described above.

Examples of the acidic substance include, but are not limited to, hydrochloric acid, sulfuric acid, nitric acid, phosphoric acid, lactic acid, acetic acid, formic acid, and citric acid. Hydrochloric acid, sulfuric acid and nitric acid are preferred, and hydrochloric acid is more preferred.

The method of adjusting the pH with an acidic substance is not particularly limited, and examples thereof include a method of appropriately adding and mixing an acidic substance at an appropriate concentration while checking the pH. It may be a continuous manner, in which an alkaline extract is continuously fed during pH adjustment and the liquid after the pH adjustment is continuously extracted, or a batch manner.

The temperature during the pH adjustment is not particularly limited but is 20° C. or higher and 100° C. or lower, preferably 20° ° C. or higher and 60° C. or lower, and more preferably 30° C. or higher and 60° ° C. or lower.

The pH adjusting range is usually 3.2 or more and 4.5 or less, preferably 3.3 or more and 4.5 or less, more preferably 3.3 or more and less than 4.0, even more preferably 3.5 or more and 4.0 or less, still more preferably 3.5 or more and less than 4.0.

The enzyme having cellobiohydrolase activity refers to an exo-type enzyme that degrades a cellulose chain of $\beta$-1,4 linked glucose from the terminal to produce cellobiose. The activity of cellobiohydrolase can be measured as the enzyme activity to degrade 4-nitrophenyl-$\beta$-D-lactopyranoside. The amount of enzyme that produces 1 μmoL of 4-nitrophenol per minute is defined as 1 U. The enzyme activity is measured by a method according to the procedure described in Reference Example 2 below. An enzyme having a cellobiohydrolase activity of 5 U/g or more is defined as an enzyme having cellobiohydrolase activity, and a cellobiohydrolase activity value of the enzyme is preferably 5 to 1,000 U/g, more preferably 5 to 500 U/g, even more preferably 10 to 500 U/g, and particularly preferably 20 to 300 U/g.

The enzyme having xylanase activity refers to an endo-type enzyme that randomly degrades xylan of $\beta$-1,4-linked xylose. Although the activity of xylanase may be determined by measuring the amount of reducing sugar contained in a post-reaction liquid using commercially available xylan as a reagent (e.g., Birchwood xylan) as a substrate, it is preferable to use "Xylanase Assay Kit (XylX6 Method) from Megazyme Ltd. In the "Xylanase Assay Kit (XylX6 Method)," the XylX6 reagent is decomposed by a combination of xylanase in the analyte and $\beta$-xylosidase as an auxiliary reagent to produce 4-nitrophenol, whereby the activity of xylanase can be measured. The amount of enzyme that produces 1 μmoL of 4-nitrophenol per minute is defined as 1 U. The enzyme activity is measured by a method according to the procedure described in Reference Example 3 below. An enzyme having a xylanase activity of 400 U/g or more is defined as an enzyme having xylanase activity. The xylanase activity value is preferably 400 to 50,000 U/g, more preferably 500 to 50,000 U/g, even more preferably 1,000 to 50,000 U/g, and particularly preferably 3,000 to 45,000 U/g.

The enzyme is produced by a microorganism and, for example, may be produced by a single microorganism or a plurality of microorganisms. Examples of microorganisms that produce cellobiohydrolase and xylanase include microorganisms of the genera *Trichoderma, Aspergillus, Cellulomonas, Clostridium, Streptomyces, Humicola, Acremonium, Irpex, Mucor,* and *Talaromyces.* The genus *Trichoderma* is preferred.

The microorganism belonging to the genus *Trichoderma* is not particularly limited, but *Trichoderma reesei* is preferred and specific examples thereof include *Trichoderma reesei* QM9414, *Trichoderma reesei* QM9123, *Trichoderma reesei* Rut C-30, *Trichoderma reesei* PC3-7, *Trichoderma reesei* CL-847, *Trichoderma reesei* MCG77, *Trichoderma reesei* MCG80, and *Trichoderma viride* QM9123. In addition, microorganisms derived from the genus *Trichoderma* described above may be mutant strains, which have been subjected to a mutation treatment with a mutagen or UV irradiation to improve cellulase productivity.

The enzyme may be added in a purified form; a culture medium may be added as a crude enzyme; a commercially available cellulase agent or xylanase agent may be used; or an enzyme other than cellobiohydrolase and xylanase may be included, as long as the above activities are satisfied. For example, the enzyme may contain $\beta$-glucosidase, $\beta$-xylosidase, endoglucanase, or mannanase.

Examples of the commercially available cellulase agent or xylanase agent include "Cellic CTec" ® and "Cellic CTec2" ®, manufactured by Novozymes; "Accellerase" ® 1000, "Accellerase" ® 1500, and "Accellerase" ® DUET, manufactured by Danisco Japan Ltd.; "Cellulase from *Trichoderma reesei* ATCC 26921," "Cellulase from *Trichoderma viride,*" and "Cellulase from *Trichoderma longibrachiatum,*" manufactured by Sigma Aldrich; and "Cellulosin TP25" and "Cellulosin HC100," manufactured by HBI Enzymes Inc.

The amount of the enzyme to be added may be appropriately changed depending on the enzyme to be added and is not particularly limited. However, the amount thereof as a crude enzyme or enzyme preparation is 0.001 parts by weight to 50 parts by weight, preferably 0.005 parts by weight to 20 parts by weight, and more preferably 0.005 parts by weight to 5 parts by weight per 100 parts by weight of the pH-adjusted extract.

The expression "the extract is adjusted to have a pH within the predetermined range and reacted with the enzyme to obtain an enzyme reaction solution" means that the enzyme is present in the extract adjusted to have a pH within the predetermined range, and the enzyme may be added during the pH adjustment but is preferably added after the pH adjustment within the predetermined rang. The enzyme may be added in a continuous manner or batch manner.

The time for reacting the enzyme refers to a time during which the enzyme is present in a state of pH within the predetermined range while the solid-liquid separating treatment is performed to obtain a clear liquid. When the reaction is performed in a continuous manner, the time refers to a residence time during which the enzyme is present in a state of pH within the predetermined range while the solid-liquid separating treatment is performed to obtain a clear liquid.

The time for reacting the enzyme at a pH in the above predetermined range is not particularly limited, but preferably 5 minutes or more and 8 hours or less, more preferably 5 minutes or more and 6 hours or less, even more preferably 5 minutes or more and 4 hours or less, still more preferably 10 minutes or more and 4 hours or less, and particularly preferably 10 minutes or more and 2 hours or less.

The temperature at which the above enzyme is reacted may be appropriately changed according to the enzyme to be used, and is not particularly limited, but preferably 15° C. to 100° ° C., more preferably 30° ° C. to 60° C., and even more preferably 35° C. to 55° C.

Step (3)

According to an example, in the step (3), the enzyme reaction solution obtained in step (2) is subjected to solid-liquid separation to obtain a clear liquid containing a polyphenol-containing composition.

In the solid-liquid separating treatment of the enzyme reaction solution described above, the method of the solid-liquid separating treatment to be used is not particularly limited, but methods such as filtration, centrifugation, and sedimentation separation can be used, or a combination thereof may be used. The solid-liquid separator to be used is, for example, a sedimentation separator, a decanter-type centrifuge, a separating disc centrifuge, a screw press, a filter press, a belt press, and a belt screen, or a combination thereof. Preferred are a filter press, a decanter-type centrifuge, and a separating disc centrifuge.

Depending on the solid-liquid separating method, a filter aid may be used. Examples of the filter aid include, but are not limited to, diatomaceous earth, perlite, cellulose, and activated carbon, and diatomaceous earth is preferred. The filter aid may be added from the process of obtaining an extract to the solid-liquid separation of the enzyme reaction solution to obtain a clear liquid, and the timing of the addition is not particularly limited. The amount of the filter aid is not particularly limited but is 0.05 parts by weight to 10 parts by weight, and preferably 0.1 parts by weight to 5 parts by weight per 100 parts by weight of the enzyme reaction solution.

Step (4)

The clear liquid obtained in the step (3) may be filtered through one or more separation membranes selected from the group consisting of a microfiltration membrane, an ultrafiltration membrane, a nanofiltration membrane, and a reverse osmosis membrane to obtain a permeate and/or non-permeate containing a polyphenol-containing composition.

Further, preferably, the permeate obtained by filtering the clear liquid through a microfiltration membrane in the step (4) is filtered through one or more separation membranes selected from the group consisting of an ultrafiltration membrane, a nanofiltration membrane, and a reverse osmosis membrane to collect the non-permeate containing the polyphenol-containing composition.

Further, preferably, the clear liquid or the permeate obtained by filtration through a microfiltration membrane in the step (4) is filtered through a nanofiltration membrane to obtain a permeate containing the polyphenol-containing composition.

Hereinafter, a process of filtering the clear liquid through one or more separation membranes selected from the group consisting of a microfiltration membrane, an ultrafiltration membrane, and a nanofiltration membrane to collect a polyphenol-containing composition is described.

The microfiltration membrane refers to a membrane having an average pore size of 0.01 μm to 5 mm, which is often called microfiltration or MF membrane for short. To concentrate the solid content on the membrane surface and prevent the membrane from clogging up internally, the average pore size is preferably 0.45 μm or less, and more preferably 0.22 μm or less.

Examples of the material of the microfiltration membrane to be used include, but are not particularly limited to, celluloses, aromatic polyamide, polyvinyl alcohol, polysulfone, polyvinylidene fluoride, polyethylene, polyacrylonitrile, polypropylene, polycarbonate, polytetrafluoroethylene, ceramics, and metals.

Examples of the form of the microfiltration membrane include, but are not limited to, a hollow fiber type, a tubular type, a flat membrane type, and a spiral type. The filtration method may be dead-end filtration, cross-flow filtration, constant pressure filtration, or constant flow filtration. When clogging of the microfiltration membrane occurs, reverse washing, in which a washing liquid is passed from the permeate side to the non-permeate side of the membrane, or air washing, in which a gas is supplied to the non-permeate side of the membrane to peel off the cake formed on the membrane surface, may be carried out. Examples of the washing liquid for the reverse washing include a filtrate of the microfiltration membrane, water, and a chemical solution.

The ultrafiltration membrane refers to a membrane having a molecular weight cut-off of more than 1,000 and 200,000 or less, which is often called ultrafiltration or UF membrane for short. In the ultrafiltration membrane, the pore size is too small to measure the sizes of the pores on the membrane surface with an electron microscope or the like so that a value called the molecular weight cut-off is used as an index of the size of the pore instead of the average pore size. As described "The curve obtained by plotting the molecular weights of solutes along the abscissa and the blocking rates along the ordinate is called the molecular weight cutoff curve. The molecular weight with which the blocking rate reaches 90% is called the molecular weight cutoff." in p. 92 of The Membrane Society of Japan ed., Membrane Experiment Series, Vol. III, Artificial Membrane, editorial committee members: Shoji Kimura, Shin-ichi Nakao, Haruhiko Ohya and Tsutomu Nakagawa (1993, published by Kyoritsu Shuppan Co., Ltd.), the molecular weight cut-off is well-known to those skilled in the art as an index representing the membrane performance of an ultrafiltration membrane.

Examples of the material of the ultrafiltration membrane to be used include, but are not particularly limited to, celluloses, aromatic polyamide, polyvinyl alcohol, polysulfone, polyvinylidene fluoride, polyethylene, polyacrylonitrile, polypropylene, polycarbonate, polytetrafluoroethylene, ceramics, and metals.

Examples of the material of the ultrafiltration membrane to be used include, but are not particularly limited to, celluloses, aromatic polyamide, polyvinyl alcohol, polysulfone, polyvinylidene fluoride, polyethylene, polyacrylonitrile, polypropylene, polycarbonate, polytetrafluoroethylene, ceramics, and metals.

Examples of the form of the ultrafiltration membrane include, but are not limited to, a hollow fiber type, a tubular type, a flat membrane type, and a spiral type. The filtration method may be dead-end filtration, cross-flow filtration, constant pressure filtration, or constant flow filtration.

The nanofiltration membrane is also called a nanofilter (nanofiltration membrane or NF membrane), which is generally defined as "a membrane that allows permeation of monovalent ions but blocks divalent ions." The membrane is considered to have fine voids of about several nanometers and mainly used to block fine particles, molecules, ions and salts in water.

The material of the nanofiltration membrane to be used may be a macromolecular material such as cellulose acetate polymer, polyamide, polyester, polyimide, and vinyl polymer, and the membrane may include a plurality of membrane materials.

Examples of the form of the nanofiltration membrane include, but are not limited to, a hollow fiber type, a tubular type, a flat membrane type, and a spiral type. The filtration method may be dead-end filtration, cross-flow filtration, constant pressure filtration, or constant flow filtration.

The molecular weight cut-off of the nanofiltration membrane is usually 100 to 1,000, preferably 150 to 1,000, and more preferably 300 to 1,000. Colored substances in polyphenol components are concentrated on the non-permeate side by filtration through a nanofiltration membrane having a molecular weight cut-off of 300 to 1,000, thereby yielding polyphenol components with reduced coloration on the permeable side.

When the clear liquid is filtered through one or more separation membranes selected from the group consisting of a microfiltration membrane, an ultrafiltration membrane, and a nanofiltration membrane, the polyphenol-containing composition can be recovered as a permeate or a non-permeate of the separation membrane. The polyphenol-containing composition is preferably recovered as a permeate of the separation membrane. In addition, filtration of the clear liquid through the microfiltration membrane before filtration through the ultrafiltration membrane or nanofiltration membrane can prevent the ultrafiltration membrane or nanofiltration membrane from clogging. Further, components contained in the clear liquid may be fractionated and/or purified by combining ultrafiltration membranes and/or nanofiltration membranes having different pore sizes.

Hereinafter, a process of filtering the clear liquid through a reverse osmosis membrane to recover the polyphenol-containing composition will be described.

The reverse osmosis membrane is also called an RO membrane, which is generally defined as "a membrane having a desalination function that can also remove monovalent ions." The membrane is considered to have ultrafine voids of about several angstroms to several nanometers and mainly used for removal of ionic components such as seawater desalination and production of ultrapure water. The molecular weight cut-off thereof is less than 100.

The material of the reverse osmosis membrane to be used may be a macromolecular material such as cellulose acetate polymer, polyamide, polyester, polyimide, and vinyl polymer, and the membrane may include a plurality of membrane materials.

Examples of the form of the reverse osmosis membrane include, but are not limited to, a hollow fiber type, a tubular type, a flat membrane type, and a spiral type. The filtration method may be dead-end filtration, cross-flow filtration, constant pressure filtration, or constant flow filtration.

The clear liquid can be filtered through the reverse osmosis membrane to concentrate polyphenol components on the non-permeate side. Depending on the type of the reverse osmosis membrane and operating conditions, impurities other than the polyphenol components may be removed to the permeate side, allowing the polyphenol components to be purified while being concentrated. In other words, when the clear liquid is filtered through the reverse osmosis membrane, the polyphenol-containing composition is recovered as the non-permeate of the separation membrane.

The clear liquid may be filtered through one or more separation membranes selected from the group consisting of a microfiltration membrane, an ultrafiltration membrane, and a nanofiltration membrane, followed by filtration of a permeate thereof through a reverse osmosis membrane to recover the polyphenol-containing composition as a non-permeate. Although the permeate obtained by filtration through the microfiltration membrane and/or ultrafiltration membrane can be filtered through the reverse osmosis membrane to concentrate the polyphenol components on the non-permeate side of the reverse osmosis membrane while preventing the reverse osmosis membrane from clogging, it is preferable to concentrate the polyphenol components on the non-permeate side of the reverse osmosis membrane by filtering at least the permeate filtered through the microfiltration membrane through the reverse osmosis membrane. Alternatively, the polyphenol components may be fractionated or purified by filtering the permeate of the nanofiltration membrane through the reverse osmosis membrane.

Polyphenol-Containing Composition

The polyphenol-containing composition derived from herbaceous biomass can be obtained by the production method as described above.

The polyphenol-containing composition derived from herbaceous biomass may contain at least coumaric acid as a polyphenol component and further contains xylose as a component other than polyphenol. Although the composition ratio of these components is not particularly limited, the content (% (w/w)) of xylose relative to coumaric acid is preferably 1% to 200% (w/w), more preferably 2% to 100% (w/w), and even more preferably 2% to 50% (w/w). In this example, an effect that coloration over time hardly proceeds can be achieved. The degree of coloration can be evaluated by the absorbance at 550 nm, and the smaller the absorbance, the lower the degree of coloration.

The polyphenol-containing composition may be in the form of a liquid or a powder, but a polyphenol-containing composition with a content of xylose relative to coumaric acid of 2 to 50% (w/w) in the form of a powder is preferred to produce the effect of no stickiness when touched by hand. Although a method of making the composition into a powder is not particularly limited, a spray drying method is preferred.

EXAMPLES

Hereinafter, our methods will be described in more detail with reference to Examples, but this disclosure is not limited to the Examples. Unless otherwise specified, the measuring method and the unit described in the specification are in accordance with the provisions of the Japanese Industrial Standard (JIS).

Reference Example 1: Measurement of Protein
Concentration

The concentration of proteins in an aqueous solution was measured using a measurement kit according to Bradford method (Quick Start Bradford Protein Assay, manufactured by Bio-Rad Laboratories, Inc.).

Reference Example 2: Measurement of
Cellobiohydrolase Activity

In 50 mM sodium acetate buffer (pH 5.0), 4-nitrophenyl-β-D-lactopyranoside (manufactured by Sigma-Aldrich) was dissolved at 1 mM to provide a substrate solution. To 90 µL of the substrate solution was added 10 µL of an appropriately diluted enzyme liquid, and the mixture was allowed to stand at 30° ° C. for reaction. After 60 minutes, 10 µL of sodium carbonate solution was added to stop the reaction and develop the color of released 4-nitrophenol, and the absorbance was measured at 405 nm. A blank used was reacted in the same manner except that the enzyme liquid was added after the addition of the sodium carbonate solution. One enzyme unit (1 U) is defined as the amount of the enzyme that produces 1 µmol of 4-nitrophenol per minute under the above conditions, and the activity per gram of protein is calculated using equations below:

Activity of cellobiohydrolase per enzyme liquid [U/mL]=(4-nitrophenol [µmol/mL]×amount of reaction liquid [µL])/(reaction time [min]× amount of enzyme liquid [µL])×dilution factor (times)

Cellobiohydrolase activity per gram of protein of enzyme [U/g]=(activity per enzyme liquid [U/mL]/protein concentration of enzyme liquid [g/L])×1,000.

Reference Example 3: Measurement of Xylanase Activity

The measurement was carried out using "Xylanase Assay Kit (XylX6 Method)" from Megazyme Ltd. First, 2.5 µL of 1M sodium acetate buffer (pH 5.0), 25 µL of a XylX6 reacting solution prepared according to the kit, and 12.5 µL of Milli-Q water were mixed, and 10 µL of an appropriately diluted enzyme liquid was added thereto. The mixture was allowed to stand at 30° C. for reaction. After 10 minutes, 100 µL of sodium carbonate solution was added to stop the reaction and develop the color of released 4-nitrophenol, and the absorbance was measured at 405 nm. A blank used was reacted in the same manner except that the enzyme liquid was added after the addition of the sodium carbonate solution. One enzyme unit (1 U) is defined as the amount of the enzyme that produces 1 µmol of 4-nitrophenol per minute under the above conditions, and the activity per gram of protein is calculated using equations below:

Activity of xylanase per enzyme liquid [U/mL]=(4-nitrophenol [µmol/mL]×amount of reaction liquid [µL])/(reaction time [min]×amount of enzyme liquid [µL])×dilution factor (times)

Xylanase activity per gram of protein of enzyme [U/g]=(activity per enzyme liquid [U/mL]/protein concentration of enzyme liquid [g/L])×1,000.

Reference Example 4: Measurement of Aromatic Compound

The concentration of an aromatic compound such as coumaric acid and ferulic acid was measured under the following conditions:

Device: HITACHI high-performance liquid chromatography, LaChrom Elite

Column: Synergi 2.5 u Hydro-RP 100A 100×3.00 mm (Phenomenex)

Mobile phase: 0.1% phosphoric acid:acetonitrile=93:7 to 5:95, gradient

Detector: Diode Array

Flow rate: 0.6 mL/min

Temperature: 40° C.

Reference Example 5: Measurement of Sugar Concentration

The xylose concentration was measured under HPLC conditions described below based on comparison with standard samples:

Column: ACQUITY UPLC BEH Amide (manufactured by Waters Corporation)

Mobile Phase A: 80% acetonitrile+0.1% TFA

Mobile Phase B: 30% acetonitrile+0.1% TFA

Flow rate: 0.12 mL/min.

The ratio of the mobile phase B was gradually increased from 0% to 40% in 10 minutes, at 10.01 minutes, only mobile phase A was used again, and the analysis was conducted up to 20 minutes.

Detecting method: ELSD (evaporative light scattering detector)

Temperature: 55° C.

Reference Example 6: Preparation of Bagasse Alkaline Extract

Bagasse, which is a residue of pressed sugar cane, was added to and mixed with a 0.45 (wt/wt) % aqueous sodium hydroxide solution to achieve 5 wt % in dry weight, and the mixture was allowed to react at 90° C. for 3 hours to separate a solid and a liquid, thus obtaining an alkaline extract as the liquid.

Reference Example 7: Measurement of Turbidity

The turbidity of the supernatant obtained by centrifuging a saccharified liquid using a high-performance laboratory turbidimeter (2100N) manufactured by HACH.

Comparative Examples 1 to 4 and Examples 1 and 2: Solid-Liquid Separability by Sedimentation The bagasse alkaline extract prepared according to Reference Example 6 was adjusted to have a pH of 3.5 using 35% (w/w) hydrochloric acid. The following enzymes were each added thereto: Enzyme 1 (with cellobiohydrolase activity and without xylanase activity), "Pectinase from *Aspergillus aculeatus*" (liquid form, manufactured by Sigma-Aldrich); Enzyme 2 (without cellobiohydrolase activity or xylanase activity), "Amyloglucosidase from *Aspergillus niger*" (liquid form, manufactured by Sigma-Aldrich); Enzyme 3 (with cellobiohydrolase activity and without xylanase activity), "Cellulosin GM5" (powder form, manufactured by HBI Enzymes Inc.); Enzyme 4 (with cellobiohydrolase activity and xylanase activity), "Cellulosin TP25" (powder form, manufactured by HBI Enzymes Inc.); and Enzyme 5 (with cellobiohydrolase activity and xylanase activity), "Accellerase DUET" (liquid form, manufactured by Danisco Japan Ltd.). Each of the enzymes was added at 0.03 g to 30 g of the extract adjusted to having a pH of 3.5.

After the addition, the reaction was carried out at 50° C. for 1 hour with stirring. Thereafter, the mixture was allowed to stand for 15 minutes, and the supernatant after sedimentation was collected to measure the turbidity according to Reference Example 7. The same operation was carried out without adding the enzymes, and if no turbid matter was precipitated, the 15 mL was collected to measure the turbidity.

The cellobiohydrolase and xylanase activities of each enzyme were measured according to Reference Examples 2 and 3.

The results are shown in Table 1. In Comparative Examples 1 to 4, the turbid matter generated by pH adjustment became a turbid micelle-like state without sedimentation, resulting in a turbidity of 1,000 or more so that the measurement could not be conducted. On the other hand, in Examples 1 and 2, the turbidity of the supernatant was significantly lower than that in Comparative Examples 1 to 4, and the solid-liquid separability by sedimentation was improved at rest.

TABLE 1

| | Enzyme added | Derivation | Cellobiohydrolase Activity (U/g) | Xylanase Activity (U/g) | Supernatant Turbidity (NTU) |
|---|---|---|---|---|---|
| Comparative Example 1 | None | | | | >1000 |
| Comparative Example 2 | Enzyme 1 | *Aspergillus* | 160 | 320 | >1000 |
| Comparative Example 3 | Enzyme 2 | *Aspergillus* | Below detection limit | Below detection limit | >1000 |
| Comparative Example 4 | Enzyme 3 | *Aspergillus* | 30 | 140 | >1000 |
| Example 1 | Enzyme 4 | *Trichoderma* | 50 | 40000 | 210 |
| Example 2 | Enzyme 5 | *Trichoderma* | 94 | 10000 | 240 |

Comparative Examples 5 and 6 and Examples 3 to 6: Solid-Liquid Separability at Different pH The enzyme was added in the same manner as in Example 1, except that the bagasse alkaline extracts were each adjusted to have a pH of 3.0, 3.3, 3.8, 4.0, 4.5, and 5.0, the mixture was allowed to stand for 15 minutes, and the supernatant after sedimentation was collected to measure the turbidity according to Reference Example 7.

The results are shown in Table 2. As shown in Table 2, the turbidity of the supernatant was lower at pH 3.3 to 4.5, and the solid-liquid separability by sedimentation at rest was improved.

TABLE 2

| | pH | Supernatant turbidity |
|---|---|---|
| Comparative Example 5 | 3.0 | 580 |
| Example 3 | 3.3 | 310 |
| Example 2 | 3.5 | 240 |
| Example 4 | 3.8 | 235 |
| Example 5 | 4.0 | 245 |
| Example 6 | 4.5 | 350 |
| Comparative Example 6 | 5.0 | 620 |

Comparative Example 7 and Examples 7 and 8: Solid-Liquid Separation with Filter Press To the bagasse alkaline extracts prepared according to Reference Example 6 was added 1 part by weight of diatomaceous earth per 100 parts by weight of the alkaline extracts, and the mixtures were each adjusted to have a pH of 3.5 and 4.5 using 35% (w/w) hydrochloric acid. To 3 L of the pH-adjusted extract was added 3 mL of Enzyme 5 (with cellobiohydrolase activity and xylanase activity), "Accellerase DUET" (liquid form, manufactured by Danisco Japan Ltd.), and the mixture was reacted at 50° C. with stirring for 30 minutes. After the reaction, solid-liquid separation was carried out with a filter press. A compact filtration device MO-4 manufactured by Yabuta Industries Co., Ltd. was used as the filter press. The solid-liquid separation with the filter press was also carried out in the same manner except that no enzyme was added to the alkali-treated liquid adjusted to have a pH of 3.5. The results are shown in Table 3.

As shown in Table 3, the filtrate volume after 5 minutes was larger in Examples 7 and 8 than in Comparative Example 7, and the solid-liquid separability by the filter press was improved. In addition, the filtrate volume was larger in Example 7 than in Example 8, and the solid-liquid separability in the filter press was improved.

TABLE 3

| | pH | Enzyme added | Filtrate volume (L) after 5 minutes |
|---|---|---|---|
| Comparative Example 7 | 3.5 | None | 0.5 |
| Example 7 | 3.5 | Yes | 2.8 |
| Example 8 | 4.5 | Yes | 1.5 |

Comparative Examples 8 to 10 and Example 9: Filtration Treatment with Microfiltration Membrane The bagasse alkaline extracts prepared according to Reference Example 6 were each adjusted to have a pH of 3.5 and 5.0 using 35% (w/w) hydrochloric acid. To 30 mL of the pH-adjusted extract was added 30 μL of Enzyme 5 (with cellobiohydrolase activity and xylanase activity), "Accellerase DUET" (liquid form, manufactured by Danisco Japan Ltd.), and the mixture was reacted at 50° ° C. with stirring for 30 minutes.

After the reaction, the mixture was centrifuged at 1,500 G for 10 minutes, and 2 mL of the supernatant subjected to microfiltration by centrifugation using Ultrafree-CL (manufactured by MILLIPORE) at 500 G for 1 minute to measure the amount of the permeate. The microfiltration was also carried out in the same manner except that no enzyme was added. The results are shown in Table 4.

As shown in Table 4, in Example 9, where the enzyme was added to the extract adjusted to have a pH of 3.5, the filtration performance on the microfiltration membrane was significantly improved compared to when the enzyme was not added. On the other hand, when the enzyme was added at pH 5.0, there was little change in filtration performance on the microfiltration membrane.

US 12,630,849 B2

15                                                                          16

TABLE 4

|  | pH | Enzyme added | Filtrate volume of microfiltration membrane (mL) |
|---|---|---|---|
| Example 9 | 3.5 | Yes | 1.5 |
| Comparative Example 8 | 5 | Yes | 0.5 |
| Comparative Example 9 | 3.5 | None | 0.3 |
| Comparative Example 10 | 5 | None | 0.2 |

Comparative Examples 11 to 15 and Examples 10 to 14: Total Circulation Filtration Treatment with Ultrafiltration Membrane, Nanofiltration Membrane, and Reverse Osmosis Membrane The bagasse alkaline extract prepared according to Reference Example 6 was adjusted to have a pH of 3.5 using 35% (w/w) hydrochloric acid. To 10 L of the pH-adjusted The permeate was also filtered through the microfiltration membrane without enzyme in the same manner except that no enzyme was added, and the permeate of the microfiltration membrane was filtered through the same type of membrane.

The results are each shown in Table 5. As shown in Table 5, both the operating pressure at the start of filtration and the operating pressure after 30 minutes were lower in the addition of the enzyme than in the addition of no enzyme, and the filtration performance was improved by the addition of the enzyme in the filtration through the ultrafiltration membrane, the nanofiltration membrane, and the reverse osmosis membrane. Although not shown in the table, the filtration rate of the microfiltration membrane with the enzyme was about 10 times that of the microfiltration membrane without enzyme.

TABLE 5

|  | Enzyme added | Membrane species | Molecular weight cut-off (Da) | Initial operating pressure (Mpa) | Operating pressure after 30 minutes (Mpa) |
|---|---|---|---|---|---|
| Example 10 | Yes | Ultrafiltration membrane | 50000 | 0.15 | 0.16 |
| Example 11 |  | Nanofiltration membrane 1 | 1000 | 0.5 | 0.6 |
| Example 12 |  | Nanofiltration membrane 2 | 600-800 | 1 | 1.1 |
| Example 13 |  | Nanofiltration membrane 3 | 300-500 | 1.5 | 1.6 |
| Example 14 |  | Reverse osmosis membrane |  | 2 | 2.2 |
| Comparative Example 11 | None | Ultrafiltration membrane | 50000 | 0.3 | 0.5 |
| Comparative Example 12 |  | Nanofiltration membrane 1 | 1000 | 2 | 3 |
| Comparative Example 13 |  | Nanofiltration membrane 2 | 600-800 | 4 | 6 |
| Comparative Example 14 |  | Nanofiltration membrane 3 | 300-500 | 6 | Not Work |
| Comparative Example 15 |  | Reverse osmosis membrane |  | Not Work | Not Work | extract was added 10 mL of Enzyme 5 (with cellobiohydrolase activity and xylanase activity), "Accellerase DUET" (liquid form, manufactured by Danisco Japan Ltd.), and the mixture was reacted at 50° C. with stirring for 30 minutes. After the reaction, the mixture was allowed to stand to obtain a supernatant. The supernatant was filtered using a microfiltration membrane, "SPV0.2" (manufactured by Synder Filtration, Inc., pore size: 0.2 μm) at a membrane linear rate of 20 cm/sec.

The permeates of the microfiltration membrane were each filtered through an ultrafiltration membrane, "SPE50" (manufactured by Synder Filtration, Inc., molecular weight cut-off: 50,000 DA); a nanofiltration membrane 1, "SPE1" (manufactured by Synder Filtration, Inc., molecular weight cut-off: 1,000 DA); a nanofiltration membrane 2, "NFG" (manufactured by Synder Filtration, Inc., molecular weight cut-off: 600 to 800 DA); a nanofiltration membrane 3: "NFW" (manufactured by Synder Filtration, Inc., molecular weight cut-off: 300 to 500 DA); and a reverse osmosis membrane, "BW60-1812-75" (obtained from a module manufactured by Filmtec, salt-blocking rate: 99%). All types of separation membranes were subjected to total circulation filtration, in which the filtrate was returned to a feed tank at a membrane linear rate of 20 cm/sec and a filtration flux of 0.5 m/D and the operating pressure at the start of filtration and 30 min after the start of filtration were measured.

Comparative Examples 16 to 19 and Examples 15 to 18: Filtration Treatment with Microfiltration Membrane, Nanofiltration Membrane, and Reverse Osmosis Membrane The bagasse alkaline extracts prepared according to Reference Example 6 were each adjusted to have a pH of 3.5 and 5.0 using 35% (w/w) hydrochloric acid. To 10 L of the pH-adjusted extract was added 10 mL of Enzyme 5 (with cellobiohydrolase activity and xylanase activity), "Accellerase DUET" (liquid form, manufactured by Danisco Japan Ltd.), and the mixture was reacted at 50° C. with stirring for 30 minutes. After the reaction, the mixture was allowed to stand to obtain a supernatant. The supernatant was filtered using a microfiltration membrane, "SPV0.2" (manufactured by Synder Filtration, Inc., pore size: 0.2 μm) at a membrane linear rate of 20 cm/sec.

The permeates of the microfiltration membrane were each filtered through a nanofiltration membrane 2, "NFG" (manufactured by Synder Filtration, Inc., molecular weight cut-off: 600 to 800 DA); a nanofiltration membrane 3: "NFW" (manufactured by Synder Filtration, Inc., molecular weight cut-off: 300 to 500 DA); and a reverse osmosis membrane, "BW60-1812-75" (obtained from a module manufactured by Filmtec, salt-blocking rate: 99%). Constant flow filtration was carried out with all types of separation membranes at a membrane linear rate of 20 cm/sec and a filtration flux of 0.2 m/D. The operating pressure was limited to 6 MPa, and when 6 MPa was reached, the filtration was switched to constant pressure filtration at 6 MPa for concentration. The permeate was also filtered through the microfiltration membrane without enzyme in the same manner except that no enzyme was added, and the permeate of the microfiltration membrane was filtered through the same type of membrane.

The permeate of the microfiltration membrane, the permeate of the nanofiltration membranes 2 and 3, and the non-permeate of the reverse osmosis membrane were each evaluated for coloration by visual inspection and measured with a spectrophotometer to quantify the evaluation. The measurement was taken immediately after preparation and 7 days after preparation. The absorbance of the liquid was The results are shown in Table 6. As shown in Table 6, the filtration through the nanofiltration membrane having a molecular weight cut-off of less than 1,000 resulted in no visible coloration of the permeate of the nanofiltration membrane and increased amount of absorption by the spectrophotometer. Thus, the permeate could be decolorized. The change in the amount of absorption by the spectrophotometer after the preparation was smaller in the enzyme-added ones than in those without enzyme.

In addition, the dried powder obtained by adding the enzyme had no stickiness upon contact.

TABLE 6

| | Addition of enzyme | Filtration 1 | Filtration 2 | Xylose content relative to coumaric acid (w/w %) | Coloration by visual inspection | Absorbance (Abs) Post preparation | 7 days later | Stickiness of dry powder |
|---|---|---|---|---|---|---|---|---|
| Example 15 | Yes | Microfiltration membrane | None | 50 | Yes | 0.100 | 0.108 | No |
| Example 16 | | Microfiltration membrane | Nanofiltration membrane 2 | 15 | No | 0.000 | 0.003 | No |
| Example 17 | | Microfiltration membrane | Nanofiltration membrane 3 | 2 | No | 0.000 | 0.002 | No |
| Example 18 | | Microfiltration membrane | Reverse osmosis membrane | 45 | Yes | 0.000 | 0.001 | No |
| Comparative Example 16 | No | Microfiltration membrane | None | 0 | Yes | 0.100 | 0.130 | Yes |
| Comparative Example 17 | | Microfiltration membrane | Nanofiltration membrane 2 | 0 | No | 0.001 | 0.010 | Yes |
| Comparative Example 18 | | Microfiltration membrane | Nanofiltration membrane 3 | 0 | No | 0.000 | 0.008 | Yes |
| Comparative Example 19 | | Microfiltration membrane | Reverse osmosis membrane | 0 | No | 0.000 | 0.004 | Yes | measured with a spectrophotometer UV-1280 (manufactured by Shimadzu Corporation) using the wavelength at 550 nm as an index, which was a peak characteristic of the difference in the chromaticity measurement.

In addition, the permeate of the microfiltration membrane, the permeate of the nanofiltration membranes 2 and 3, and the non-permeate of the reverse osmosis membrane were each subjected to a spray drying method to form a powder. To evaluate the degree of stickiness of the resulting powder, the powder was left on a laboratory table in a room for 1 hour, and then the stickiness of the powder was evaluated using as an index whether the powder adhered to the hand when pressed by the finger.

Furthermore, the concentrations of coumaric acid and xylose in the permeate of the microfiltration membrane, the permeate of the nanofiltration membranes 2 and 3, and the non-permeate of the reverse osmosis membrane were measured by the methods of Reference Example 4 and Reference Example 5 to measure the xylose content (% (w/w)) relative to coumaric acid according to an equation below:

Xylose content relative to coumaric acid (%)=xylose concentration (w/v)/coumaric acid concentration (w/v)×100.

CROSS-REFERENCE TO RELATED APPLICATION

This application claims the priority based on Japanese Patent Application No. 2021-58651 filed on Mar. 30, 2021, the disclosure of which is incorporated herein by reference in its entirety.

The invention claimed is:

1. A polyphenol-containing composition comprising coumaric acid and xylose, wherein the content of the xylose relative to the coumaric acid is 1 to 200% (w/w), and the polyphenol-containing composition is an enzyme-treated alkaline extract of herbaceous biomass; wherein the enzyme has cellobiohydrolase activity and/or xylanase activity.

2. The polyphenol-containing composition according to claim 1, wherein the content of the xylose relative to the coumaric acid is 2 to 50% (w/w).

3. The polyphenol-containing composition according to claim 1, wherein the enzyme is an enzyme having cellobiohydrolase activity and xylanase activity.

4. The polyphenol-containing composition according to claim 2, wherein the enzyme is an enzyme having cellobiohydrolase activity and xylanase activity.

* * * * *